(12) United States Patent
Klausen

(10) Patent No.: US 9,788,932 B2
(45) Date of Patent: Oct. 17, 2017

(54) VASCULAR FILTER

(71) Applicant: COOK MEDICAL TECHNOLOGIES LLC, Bloomington, IN (US)

(72) Inventor: Kasper Klausen, Lille Skensved (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 391 days.

(21) Appl. No.: 14/662,802

(22) Filed: Mar. 19, 2015

(65) Prior Publication Data
US 2015/0265390 A1 Sep. 24, 2015

(30) Foreign Application Priority Data

Mar. 19, 2014 (GB) .................................. 1404928.2

(51) Int. Cl.
*A61M 29/00* (2006.01)
*A61F 2/01* (2006.01)
(52) U.S. Cl.
CPC ............ *A61F 2/01* (2013.01); *A61F 2002/011* (2013.01); *A61F 2002/018* (2013.01); *A61F 2230/0093* (2013.01)
(58) Field of Classification Search
CPC .................. A61F 2/01; A61F 2002/016; A61F 2002/018; A61F 2/013; A61F 2002/015
See application file for complete search history.

(56) References Cited

U.S. PATENT DOCUMENTS

| 4,643,184 | A | 2/1987 | Mobin-Uddin | |
|---|---|---|---|---|
| 5,324,304 | A | 6/1994 | Rasmussen | |
| 5,776,162 | A | 7/1998 | Kleshinski | |
| 7,625,390 | B2 * | 12/2009 | Hendriksen | A61F 2/01 606/200 |
| 7,699,867 | B2 * | 4/2010 | Hendriksen | A61F 2/01 606/200 |
| 7,972,353 | B2 * | 7/2011 | Hendriksen | A61F 2/01 606/200 |
| 8,043,322 | B2 * | 10/2011 | Hendriksen | A61F 2/01 606/200 |
| 8,062,328 | B2 * | 11/2011 | Hallisey | A61F 2/01 606/200 |
| 8,105,349 | B2 * | 1/2012 | Hendriksen | A61F 2/01 606/200 |

(Continued)

FOREIGN PATENT DOCUMENTS

WO    WO 2007/106378 A2    9/2007

OTHER PUBLICATIONS

Communication from the European Patent Office for EP 15275061.8, dated Sep. 5, 2016.
(Continued)

*Primary Examiner* — Jonathan Miles
(74) *Attorney, Agent, or Firm* — Brinks Gilson & Lione

(57) ABSTRACT

A filter comprises an inner, anchoring basket arranged concentrically inside an outer, alignment basket. The anchoring basket comprises a plurality of anchoring struts terminating in barbs. The alignment basket includes a plurality of alignment struts, which terminate downstream of the anchoring struts. A lumen is provided through hubs of the filter so that the filter can be deployed over a guidewire.

18 Claims, 7 Drawing Sheets

(56) References Cited

U.S. PATENT DOCUMENTS

| | | | |
|---|---|---|---|
| 8,246,648 B2* | 8/2012 | Tekulve | A61F 2/01 606/200 |
| 8,317,818 B2* | 11/2012 | Kashkarov | A61F 2/01 606/200 |
| 2002/0193828 A1* | 12/2002 | Griffin | A61F 2/01 606/200 |
| 2004/0186510 A1* | 9/2004 | Weaver | A61F 2/01 606/200 |
| 2005/0234503 A1 | 10/2005 | Ravenscroft et al. | |
| 2005/0288704 A1* | 12/2005 | Cartier | A61F 2/01 606/200 |
| 2006/0079928 A1* | 4/2006 | Cartier | A61F 2/01 606/200 |
| 2006/0100660 A1* | 5/2006 | Osborne | A61F 2/01 606/200 |
| 2006/0206138 A1 | 9/2006 | Eidenschink | |
| 2007/0167974 A1* | 7/2007 | Cully | A61B 17/221 606/200 |
| 2007/0173885 A1 | 7/2007 | Cartier et al. | |
| 2007/0198050 A1* | 8/2007 | Ravenscroft | A61F 2/01 606/200 |
| 2008/0119886 A1* | 5/2008 | Greenhalgh | A61B 17/0057 606/200 |
| 2008/0167679 A1* | 7/2008 | Papp | A61B 17/221 606/200 |
| 2008/0275495 A1 | 11/2008 | Silver | |
| 2009/0287242 A1* | 11/2009 | Cartier | A61F 2/01 606/200 |
| 2010/0318115 A1* | 12/2010 | Chanduszko | A61F 2/01 606/200 |
| 2011/0196468 A1* | 8/2011 | Brandeis | A61B 17/12022 623/1.1 |
| 2012/0089173 A1* | 4/2012 | Tekulve | A61F 2/01 606/200 |
| 2012/0184984 A1 | 7/2012 | Koehler | |
| 2013/0103073 A1* | 4/2013 | Honeycutt | A61F 2/01 606/200 |
| 2014/0172007 A1* | 6/2014 | McKinnis | A61F 2/01 606/200 |

OTHER PUBLICATIONS

Extended European Search Report for EP 15275061.8, dated Sep. 4, 2015.
Search and Examination Report for GB1404928.2, dated Oct. 2, 2014.

* cited by examiner

VASCULAR FILTER

CROSS-REFERENCE TO RELATED APPLICATIONS

This application claims the benefit of priority under 35 U.S.C. §119(a) to Great Britain Patent Application No. 1404928.2, filed Mar. 19, 2014, which is incorporated by reference here in its entirety.

TECHNICAL FIELD

The present invention relates to a vascular filter and a method of manufacture thereof. In particular it relates to a vascular filter for implantation in the inferior vena cava.

Background Art

Filtering devices that are percutaneously placed in the vena cava have been available for a number of years. A need for filtering devices arises in trauma patients, orthopaedic surgery patients, neurosurgery patients, or in patients having medical conditions requiring bed rest or non-movement because of the likelihood of thrombosis in the peripheral vasculature of patients. The thrombi may break away from the vessel wall, and, depending on the size of the thrombi, pose a serious risk of pulmonary embolism when blood clots migrate from the peripheral vasculature through the heart and into the lungs.

Examples of known filters are disclosed in U.S. Pat. No. 4,643,184, U.S. Pat. No. 5,776,162, US 2006/0100660, US 2006/0206138, US 2007/0173885, WO 2007/106378, and US 2008/0275495.

DISCLOSURE OF THE INVENTION

According to a first aspect of the present invention, there is provided a vascular filter, the filter having a collapsed configuration and an expanded configuration, the filter including: a first basket including a plurality of first legs cut from a first tube and extending from a first hub, the first hub including an uncut portion of the first tube; a second basket including a plurality of second legs cut from a second tube and extending from a second hub, the second hub including an uncut portion of the second tube; wherein the first hub is disposed concentrically within the second hub to form a filter hub, such that the pluralities of legs nest within one another; wherein the filter has a first end, the filter hub being located at or towards the first end, and a second end, the first legs terminating at the second end in the expanded configuration; wherein the second legs terminate at a position intermediate the first end and the second end in the expanded configuration, and wherein there are a greater number of second legs than first legs; and a lumen extending through the hubs to receive a guidewire during deployment.

In an embodiment, a retrieval hook is provided on the filter hub. The retrieval hook may include a partial transverse cut in the filter hub.

The first legs may include hooks or barbs at their ends.

Each plurality of legs may have a substantially similar radial outer extent in the expanded configuration, the radial outer extent of the second legs being at a position intermediate the first end and the position of the radial outer extent of the first legs. In an embodiment, the radial outer extent of the plurality of first legs is located at the second end of the filter in the expanded configuration.

Each first leg may be positioned between a pair of second legs in the expanded configuration.

The first tube may have a thicker wall than the second tube and the first legs may thus be thicker than the second legs.

The first and second hubs may be fixed to one another to form the filter hub. There may be an interference fit between the first hub and the second hub. The first and second hubs may be integral with one another to form the filter hub. The first and second hubs may be welded together to form the filter hub.

The filter may be able to self-expand from its collapsed configuration to its expanded configuration. It may include a shape-memory material, for example, Elgiloy or Nitinol, having the shape-memory of the expanded configuration.

The pluralities of legs may be laser cut from the tubes.

The first tube and the second tube may be of different materials.

According to another aspect of the present invention, there is provided a method of manufacturing a filter for capturing blood clots in a vessel, including: cutting a first plurality of legs from a first tube, leaving an uncut portion of the first tube to form a first hub; cutting a second plurality of legs from a second tube, leaving an uncut portion of the second tube to form a second hub, wherein the second plurality is greater in number than the first plurality; arranging the first hub concentrically inside the second hub to form a filter hub, with the first plurality of legs and the second plurality of legs extending in a same direction, and such that a passageway extends through the filter hub to receive a guidewire during deployment; and forming a basket shape with the first plurality of legs and forming a basket shape with the second plurality of legs.

The method may include fixing the first and second hubs to one another. An interference fit may be provided between the first hub and the second hub to form the filter hub. The first and second hubs may be integrally fixed to one another to form the filter hub. The first and second hubs may be welded together to form the filter hub.

The tubes may include a shape-memory material, such as Elgiloy or Nitinol, and the method may include treating the pluralities of legs to provide shape memory of the basket shapes.

Each plurality of legs may have a substantially similar radial outer extent in the expanded configuration, the radial outer extent of the second legs being at a position intermediate the first end and the position of the radial outer extent of the first legs.

The method may include forming a retrieval hook on the filter hub, for example by making a transverse cut in the filter hub.

The method may include using a laser to cut the legs from the tubes.

The first tube and the second tube may be of different materials.

According to a third aspect of the present invention, there is provided a method of deploying a filter as specified above in a blood vessel for capturing blood clots, including: inserting a guide wire into a blood vessel, the guide wire having a proximal end and a distal end, the proximal end being external to the vessel and the distal end being near the deployment location for the filter; deploying a sheath over the guide wire, the sheath having a proximal end and a distal end; inserting the filter into the proximal end of the sheath, the guide wire extending through the passageway provided in the hubs; and pushing the filter through the sheath until the filter exits the distal end of the sheath and expands to an expanded configuration.

BRIEF DESCRIPTION OF THE DRAWINGS

An embodiment of the present invention is described below, by way of example only, with reference to the accompanying drawings, in which.

DESCRIPTION OF THE PREFERRED EMBODIMENT

It is to be understood that the Figures are schematic and do not show the various components in their actual scale. In many instances, the Figures show scaled up components to assist the reader.

In this description, the term distal, when used with respect to the filter or a component thereof, denotes an end that it is downstream with respect to blood flow. The term proximal is used to denote an end that is upstream with respect to blood flow. However, when referring to an elongated device such as a sheath or guide wire, the term distal is used to refer to an end of a component which in use is furthest from the surgeon during the medical procedure, including within a patient. The term proximal is used to refer to an end of a component closest to the surgeon and in practice in or adjacent an external manipulation part of the device.

Known vascular filters are typically in the form of a wire mesh or basket having a conical shape. Such filters, however, usually cannot be delivered using an over-the-wire method. Furthermore, prior art filters are generally bulky and cannot be tightly compressed for delivery. Although it is known to manufacture filters by cutting struts from a tube using a laser, to date, such filters do not include sufficient struts to provide effective filtering. Moreover, these filters are at risk of tilting within the blood vessel after deployment.

Figure 1:
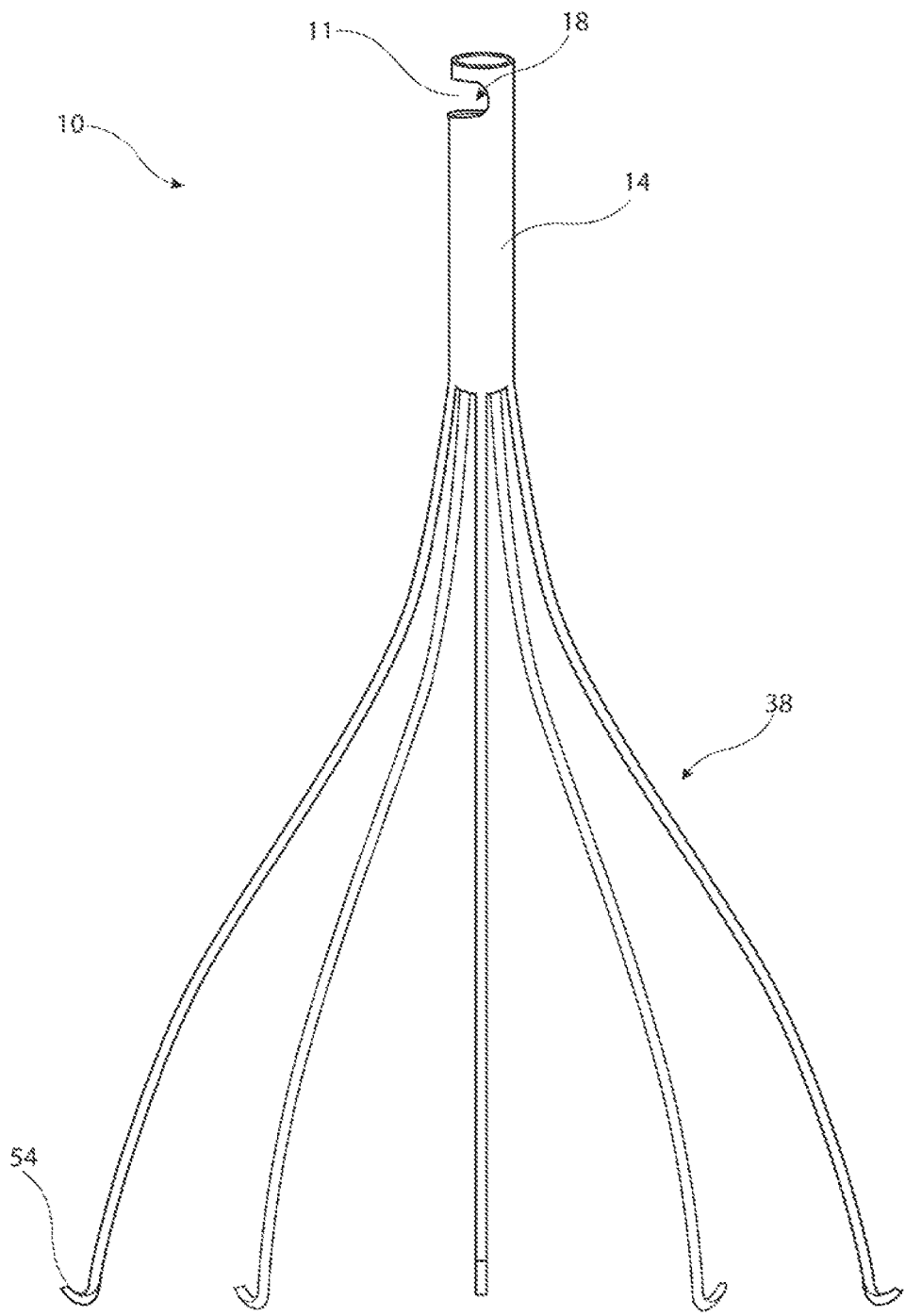
FIG. 1 illustrates an example of an anchoring basket.
Figure 2:
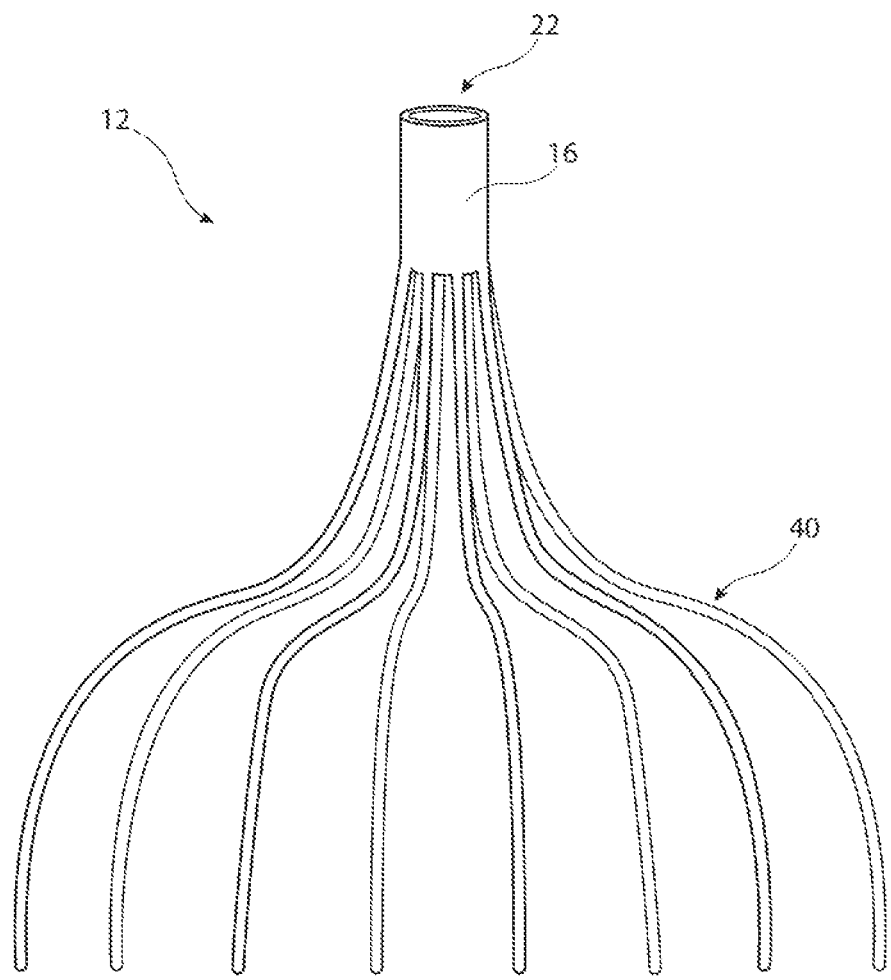
FIG. 2 illustrates an example of an alignment basket.
Figure 3:
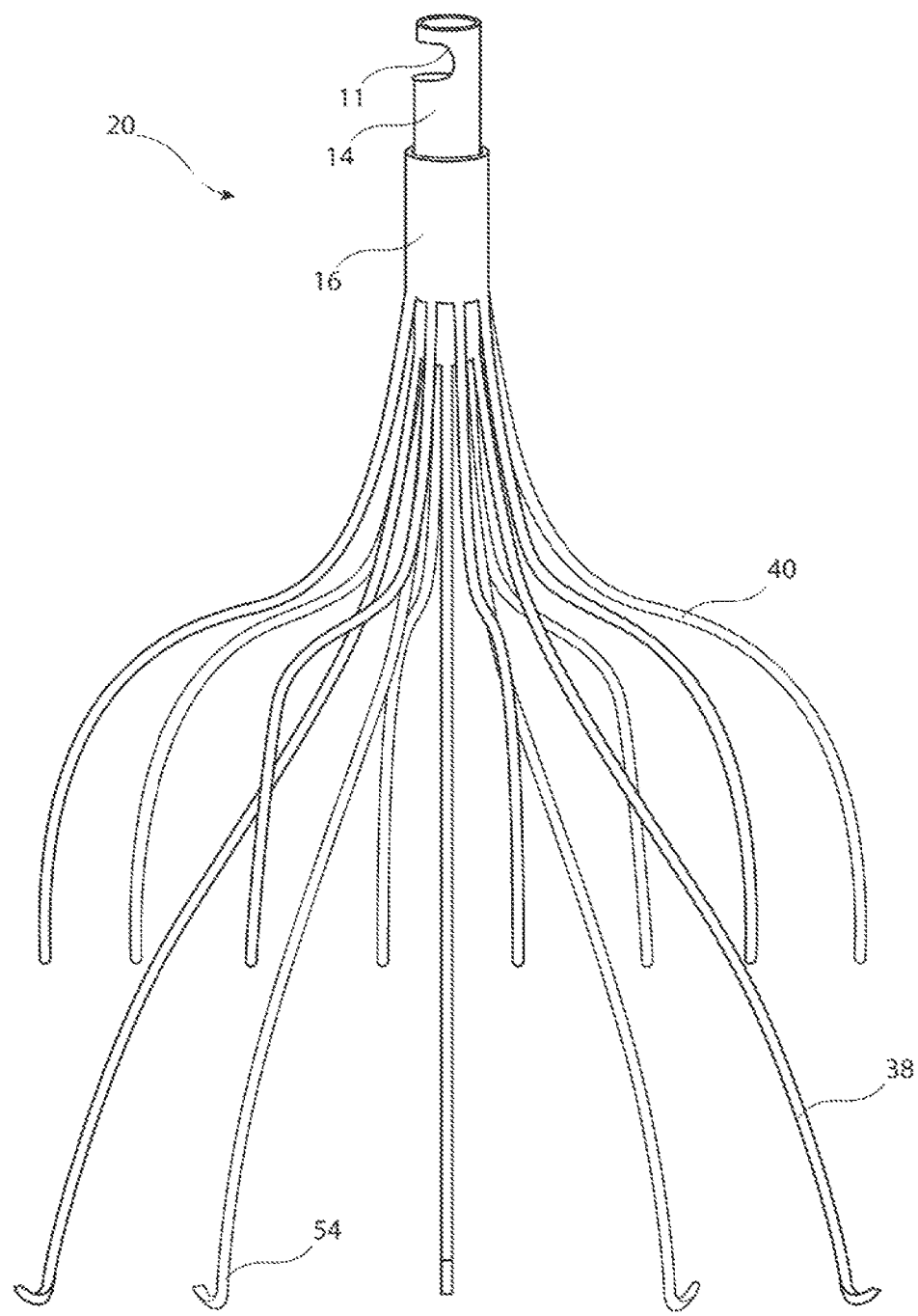
FIG. 3 illustrates an embodiment of an assembled filter including the baskets of FIGS. 1 and 2.

FIGS. 1 to 3 illustrate the components (FIGS. 1 and 2) of an embodiment of a filter 20 (shown assembled in FIG. 3). The filter 20 includes an anchoring basket 10 (shown in FIG. 1) and an alignment basket 12 (shown in FIG. 2).

The anchoring basket 10 includes a first hub 14 at its distal end. Upstream of the hub there are formed five anchoring struts 38, each of which terminates in a barb 54. The first hub 14 and the anchoring struts 38 are formed by providing five longitudinal cuts within the wall of a tube, preferably using a laser. The cuts are approximately evenly spaced around the circumference of the tube. The anchoring struts 38 are thus formed between each longitudinal cut. The cuts extend from the proximal end of the tube, however, they do not reach the distal end. A portion of the tube at the distal end thus remains uncut, thereby forming the first hub 14. In an embodiment, the tube is between 4 to 6 cm in length. The length of the uncut portion of the tube forming the first hub 14 may be approximately 5 to 15 mm. As the anchoring basket 10 is cut directly from a tube, a lumen 18 extends through the first hub 14.

In this embodiment, a notch 11 is formed towards the distal end of the first hub 14 by removing a section of the wall of the first hub 14, to leave a hook-like structure at the distal end of the first hub 14.

The tube is formed from a shape-memory material, such as Elgiloy or Nitinol. After being cut from the tube, the anchoring struts 38 are treated in a known manner to provide them with a shape memory of a basket configuration. In its expanded, basket configuration, the anchoring struts 38 extend gradually away from the longitudinal axis of the anchoring basket 10, at an angle of approximately 30 degrees for around the distal-most third of their lengths. The central third of the lengths of the anchoring struts 38 extend away from the longitudinal axis of the anchoring basket 10 at an angle of approximately 45 degrees. The proximal third of the lengths of the anchoring struts 38 turn back towards the longitudinal axis of the anchoring basket 10 such that the distal barbed ends of the anchoring struts 38, in use, engage the interior wall of the blood vessel 36 into which the filter 20 is to be deployed. In its expanded configuration, the total length of the anchoring basket 10 may be between approximately 38 and 52 mm. For example, it may have a length of approximately 45 mm. Its diameter at the proximal end (i.e. its widest point) may be between approximately 30 mm or 33 mm and 37 mm or 40 mm. For example it may be approximately 35 mm or 36 mm, although the diameter of the proximal end of the anchoring basket in situ could be anything from approximately 15 mm to approximately 30 mm according to the diameter of the vessel in which it is deployed. The thickness of the wall of the tube from which the anchoring basket 12 is cut may be approximately 0.4 to 0.55 mm. Prior to expansion the tube may have an outer diameter of approximately 1.3 or 1.5 mm to 2.2 or 2.5 mm, and may have a lumen to accommodate a 0.0035 inch (0.089 mm) wire.

FIG. 2 illustrates the alignment basket 12. Similarly to the anchoring basket 10 of FIG. 1, the alignment basket 12 is formed by cutting a tube, preferably using a laser. The tube has a larger diameter than the tube from which the anchoring basket 10 is formed. Specifically, the inner diameter of the tube from which the alignment basket 12 is formed is greater than the outer diameter of the tube from which the anchoring basket 10 is formed. For example, the inner diameter may be 1.5 mm or more. Furthermore, the tube from which the alignment basket 12 is formed preferably has a thinner wall than the tube from which the anchoring basket 10 is formed, so as to minimise the overall diameter of the filter 20 in its compressed configuration. For example, the wall of the tube from which the alignment basket 12 is formed may be in the range 0.2 to 0.3 mm.

The alignment basket 12 includes eight alignment struts 40. These are therefore formed by providing eight longitudinal cuts within the tube, extending from the proximal end of the tube to near the distal end of the tube. The tube may be approximately 35 to 40 mm in length. An uncut portion of approximately 1 to 3 mm at the distal end of the tube forms a second hub 16.

Again, a second lumen 22 is formed within the second hub 16. In view of the relative diameters of the two tubes, the second lumen 22 is sized such that the first hub 14 can fit within.

As with the anchoring basket 10, the tube from which the alignment basket 12 is formed is preferably of a shape-memory material such as Elgiloy or Nitinol. The alignment struts 40 are treated to provide them with memory of an expanded, basket configuration in a known manner. In the expanded configuration, the distal halves of the alignment struts 40 extend in a proximal direction gradually away from the longitudinal axis of the alignment basket 12 (at an angle of approximately 30°), then extend radially outwardly at an angle near perpendicular to the longitudinal axis of the alignment basket 12, finally turning approximately 90° such that the proximal ends of the alignment struts 40 are substantially parallel with the longitudinal axis of the alignment basket 12, and are spaced from the central axis of the alignment basket 12 by a distance approximately equal to or slightly greater than the radius of the vessel into which it is intended to be implanted. In one practical example, the diameter of the alignment basket 12 is approximately 33 to 37 mm at its widest point (for example, approximately 35 mm) when expanded, but may be compressed to have a diameter of approximately 15 mm during in vivo use. Its length may be approximately 25 to 35 mm (for example, approximately 30 mm).

To minimise the trauma to the vena cava caused by removing the filter 20, the free ends 60 of the alignment struts 40 preferably do not have anchoring hooks or barbs.

FIG. 3 illustrates the assembled filter 20. To assemble the filter 20, the first hub 14 is located within the second lumen 22 of the second hub 16 such that the anchoring struts 38 and the alignment struts 40 extend in a proximal direction away from the hubs 14, 16. The hubs 14, 16 are then welded together using a laser to form a single integral hub.

The assembled filter 20 thus has two layers or planes of struts 38, 40 longitudinally engaging the vessel wall. The proximal ends of the alignment struts 40 are located longitudinally between the hubs 14, 16 and the barbs 54 of the anchoring struts 38. The length of the anchoring struts 38 in their expanded configuration defines the length of the filter 20, since the alignment struts 40 in their expanded configuration do not extend further upstream than the anchoring struts 38. That is, the alignment struts 40 do not add to the overall length of the filter. In some embodiments, the length of the filter 20 is between about 3 cm and 7 cm. In a particular embodiment, the length of the filter is about 5 cm.

The anchoring struts 38 have sufficient spring strength to move the barbs 54 to the interior wall of the blood vessel where they anchor into the interior wall of the blood vessel to prevent the filter 20 from migrating from the delivery location of the filter in the blood vessel. It can be seen from the Figures that the alignment struts 40 are bent to a greater extent than the anchoring struts 38. These provide stabilising support for the filter 20, ensuring better orientation within the vessel than prior art devices.

The arrangement of the alignment struts 40 means that the radial outer extent of the alignment basket 12 is located between the radial outer extent of the anchoring basket 10 and the hubs 14, 16. This provides two spaced vessel contact points, which stabilise the filter in vivo.

The above-described filter 20 can be made relatively simply from two tubes resulting in faster and cheaper manufacture. The resulting filter 20 includes a first lumen 18 extending through the first, inner hub 14. A guidewire 66 can extend through the first lumen 18, enabling the filter 20 to be deployed over-the-wire. Furthermore, the design of the filter 20 enables it to be compressed to a very small diameter facilitating deployment. Forming the anchoring basket 10 and the alignment basket 12 from two separate tubes enables sufficient anchoring struts 38 and alignment struts 40 to be provided. This results in improved anchoring and alignment of the filter 20, and also improved filtering capacity. Both sets of struts 58, 40 can provide a filtering function.

A further advantage of forming each basket 10, 12 from a different tube is that the tubes can impart different properties on each set of struts 38, 40. For example, it is preferred that the tube from which the anchoring basket 10 is cut has thicker walls. This is so as to provide an increased radial force for the anchoring struts 38 against the blood vessel wall, to reduce the possibility of the filter 20 migrating from the site of deployment. The wall thickness of the tube from which the alignment basket 12 is cut may be thinner, as the same radial force is not required. Additionally/alternatively, the two tubes could be made of different materials. Furthermore, the shape of each basket may be independently set.

FIGS. 4 to 7 illustrate the deployment of the filter 20 in the vena cava 36, as performed, for example, by a medical specialist such as a physician.

Figure 4:
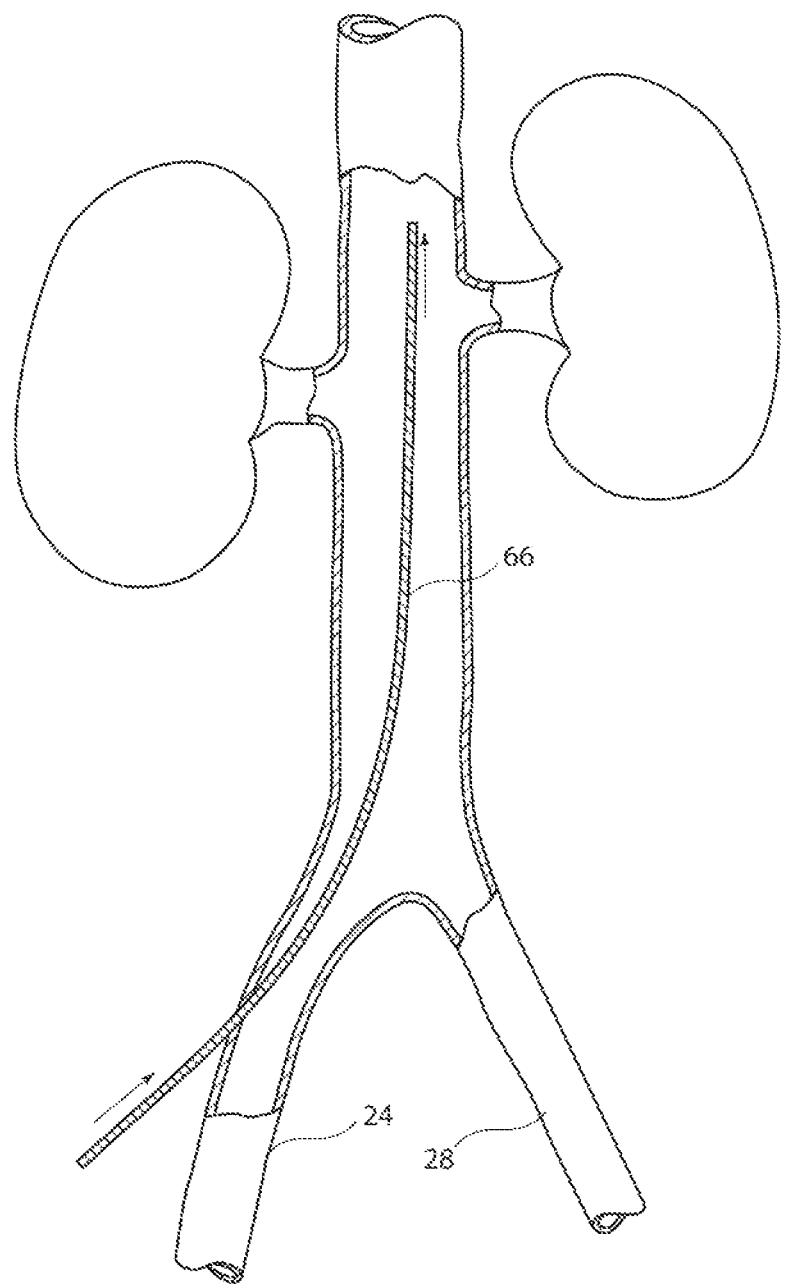
FIGS. 4 to 7 illustrate deployment of the filter over a wire into the vena cava.

Referring in particular to FIG. 4, the physician inserts a guidewire 66 through the groin using, for example, the Seldinger technique, until the distal end of the guidewire 66 is advanced beyond the inferior vena cava 36 to ensure seating of the guidewire 66.

Figure 5:
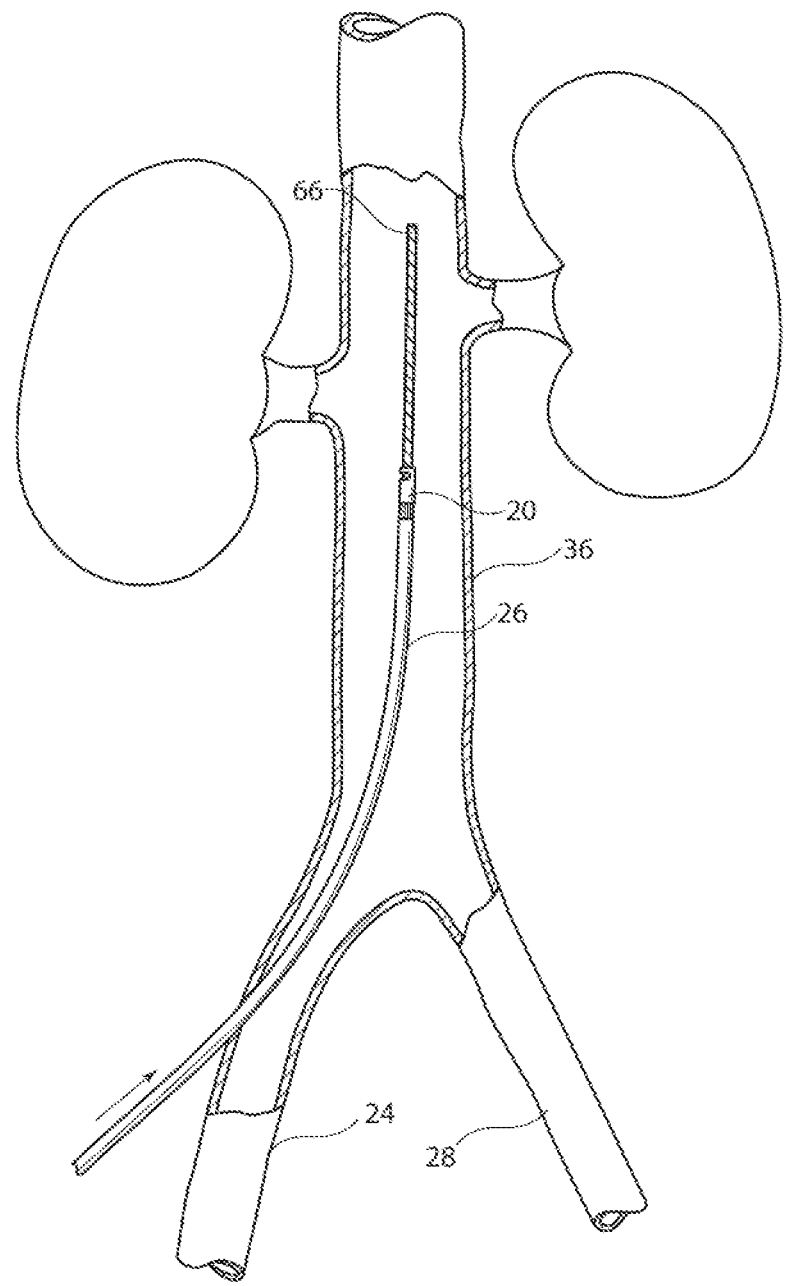

Then, as shown in FIG. 5, the physician inserts a delivery sheath 26 holding the filter 20 over the guidewire 66 through the puncture site of the patient into the iliac vein 24 and advances the sheath 26 and the filter 20 to the deployment site. Neither the sheath 26 nor the filter 20 scrapes or punctures the inner wall of the blood vessel because they follow the path of the guidewire 66. As such, the sheath 26 is deployed over the guidewire 66 so that the distal end of guidewire 66 extends beyond the distal end of the sheath 26 and the proximal end of the guidewire 66 extends beyond the proximal end of the sheath 26.

Figure 6:
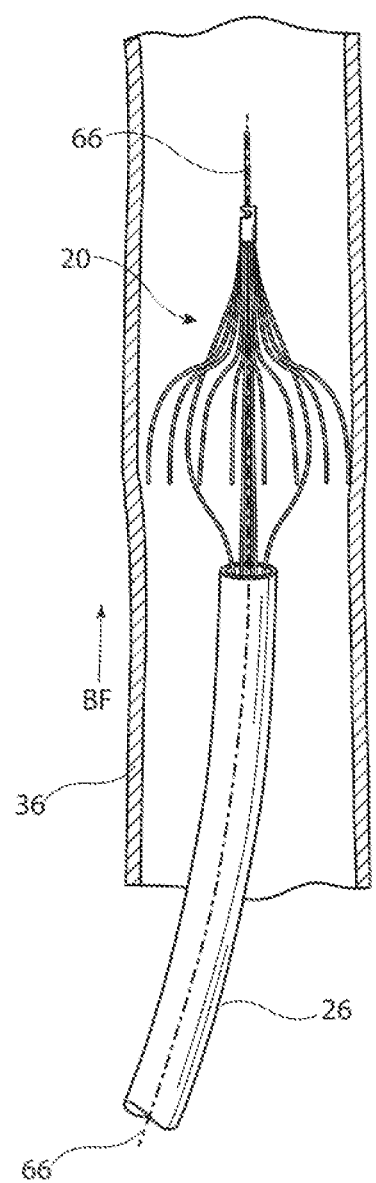

Referring to FIG. 6, the physician then pushes the filter 20 out of the distal end of the delivery sheath 26 with the free ends of the anchoring struts 38 held, for example, by a filter retainer member. The filter retainer member may be connected to a pusher member, such as a cannula, that is fed through the proximal end of the delivery sheath 26 until the filter reaches the terminal end of the delivery sheath 26. For a more complete disclosure of a filter delivery system that may be arranged to deliver the filter 20 to a desired location, reference may be made to U.S. Pat. No. 5,324,304, which is incorporated herein by reference in its entirety.

Figure 7:
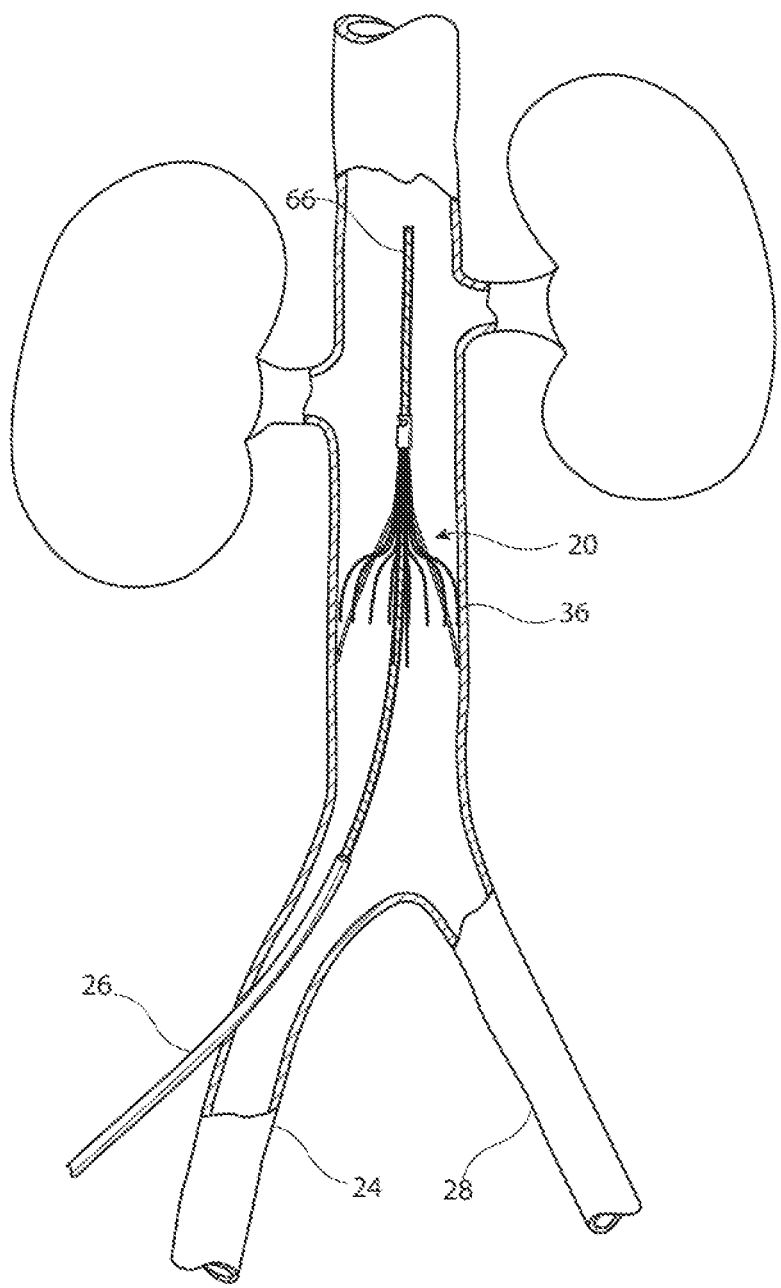

As the filter 20 emerges from the delivery sheath 26, the alignment struts 40 expand to their shape-memory expanded state to stabilise the attitude of the filter 20 about the centre of the blood vessel 36. The physician pulls the sheath 26 back to expose the barbed distal ends of the anchoring struts 38, which then assume their shape-memory expanded configuration and engage the interior wall of the blood vessel 36. The filter 20 is then fully deployed in the vena cava 36, as shown in FIG. 7, and the specialist then pulls the guidewire 66 away from the filter 20, when they are satisfied with the placement of the filter 20. The sheath 26 and the guidewire 66 are subsequently removed from the patient.

If it is desired to remove the filter 20 from the patient, for example, if the underlying medical condition has passed, this can be done by snaring the hook-like structure formed by the notch 11 in the hub 14 using a retrieval mechanism. Such a mechanism and procedure are disclosed in US 2006/0100660, which is incorporated herein by reference in its entirety.

There are various modifications that could be made to the above-described embodiment.

Although, as indicated above one or both of the basket 10, 12 may be formed by cutting tubes made of Elgiloy, other materials may also be used.

In various modifications, the anchoring struts 38 are formed from superelastic material, stainless steel wire, MP35N, Nitinol, chronichrome, cobalt chrome alloy or any other suitable material that will result in a self-opening or self-expanding filter.

The precise number of struts 38, 40 is not critical. There may be four to ten, for example four to six (for example, four or five) anchoring struts 38 and six to ten (for example, six to eight or eight to ten) alignment struts 40. However, preferably the filter 20 includes more alignment struts 40 than anchoring struts 38, possible because the alignment basket 12 is positioned concentrically outside the anchoring basket.

Although the length of the device (as dictated by the length of the anchoring basket 10) may be approximately 45 mm, in some embodiments it may be up to approximately 75 mm.

Although not necessary, in a modified version of the filter 20, the alignment struts 38 or the anchoring struts 40 could be covered by a filter mesh or filter material.

The hubs 14, 16 need not be welded together. An interference fit may be sufficient.

In summary, disclosed herein is a vascular filter which can readily be compressed for delivery. The design allows sufficient filtration struts to be provided, whilst at the same time providing anchoring and alignment functions. Cutting the device from tubes ensures a low profile and a large enough lumen to enable over-the-wire delivery.

What has been described and illustrated herein is a preferred embodiment of the invention along with some of its variations. The terms, descriptions and Figures used herein are set forth by way of illustration only and are not meant as limitations. Those skilled in the art will recognise that many variations are possible within the spirit and scope of the invention, which is intended to be defined by the following claims, and their equivalents, in which all terms are meant in their broadest reasonable sense unless otherwise indicated.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. A vascular filter, the filter having a collapsed configuration and an expanded configuration, the filter including:
    a first basket including a plurality of first legs cut from a first tube and extending from a first hub, the first hub including an uncut portion of the first tube;
    a second basket including a plurality of second legs cut from a second tube and extending from a second hub, the second hub including an uncut portion of the second tube;
    wherein the first hub is disposed concentrically within the second hub to form a filter hub, such that the pluralities of legs nest within one another;
    wherein the filter has a first end, the filter hub being located at or towards the first end, and a second end, the first legs terminating at the second end in the expanded configuration;
    wherein the second legs terminate at a position intermediate the first end and the second end in the expanded configuration, and wherein there are a greater number of second legs than first legs;
    and a lumen extending through the hubs to receive a guidewire during deployment.

2. A filter as claimed in claim 1, wherein a retrieval hook is provided on the filter hub.

3. A filter as claimed in claim 2, wherein the retrieval hook includes a partial transverse cut in the filter hub.

4. A filter as claimed in claim 1, wherein the first legs include hooks or barbs at their ends.

5. A filter as claimed in claim 1, wherein each plurality of legs has a substantially similar radial outer extent in the expanded configuration, the radial outer extent of the second legs being at a position intermediate the first end and the position of the radial outer extent of the first legs.

6. A filter as claimed in claim 5, wherein the radial outer extent of the plurality of first legs is located at the second end of the filter in the expanded configuration.

7. A filter as claimed in claim 1, wherein each first leg is positioned between a pair of second legs in the expanded configuration.

8. A filter as claimed in claim 1, wherein the first tube has a thicker wall than the second tube, the first legs thus being thicker than the second legs.

9. A filter as claimed in claim 1, wherein the first and second hubs are fixed to one another to form the filter hub.

10. A filter as claimed in claim 1, wherein there is an interference fit between the first hub and the second hub.

11. A filter as claimed in claim 1, wherein the first and second hubs are integral with one another to form the filter hub.

12. A filter as claimed in claim 11, wherein the first and second hubs are welded together to form the filter hub.

13. A filter as claimed in claim 1, wherein the filter can self-expand from its collapsed configuration to its expanded configuration.

14. A filter as claimed in claim 1, wherein the filter includes a shape-memory material having the shape-memory of the expanded configuration.

15. A filter as claimed in claim 14, wherein the shape-memory material is Elgiloy or Nitinol.

16. A filter as claimed in claim 1, wherein the pluralities of legs are laser cut from the tubes.

17. A filter as claimed in claim 1, wherein the first tube and the second tube are of different materials.

18. A method of deploying a filter as claimed in claim 1 in a blood vessel for capturing blood clots, including:
    inserting a guide wire into a blood vessel, the guide wire having a proximal end and a distal end, the proximal end being external to the vessel and the distal end being near the deployment location for the filter;
    deploying a sheath over the guide wire, the sheath having a proximal end and a distal end;
    inserting the filter into the proximal end of the sheath, the guide wire extending through the passageway provided in the hubs; and
    pushing the filter through the sheath until the filter exits the distal end of the sheath and expands to an expanded configuration.

* * * * *